United States Patent [19]
Cocilovo

[11] Patent Number: 5,843,074
[45] Date of Patent: Dec. 1, 1998

[54] THERAPEUTIC DEVICE USING PULSED AND COLORED LIGHT

[76] Inventor: Tony Cocilovo, P.O. Box 10602, Prescott, Ariz. 86304

[21] Appl. No.: 818,362

[22] Filed: Mar. 17, 1997

[51] Int. Cl.[6] .............................. A61B 17/36; A61B 5/05
[52] U.S. Cl. ............................................... 606/10; 607/90
[58] Field of Search ................................... 606/2, 10, 11, 606/13, 16, 17, 189, 204; 607/88, 89, 90, 93, 94; 128/907

[56] References Cited

U.S. PATENT DOCUMENTS

| | | | |
|---|---|---|---|
| 4,232,678 | 11/1980 | Skovajsa | 128/395 |
| 4,376,920 | 3/1983 | Smith | 333/12 |
| 4,535,784 | 8/1985 | Rohticek et al. | 128/735 |
| 4,890,898 | 1/1990 | Bentley et al. | 606/16 |
| 5,024,236 | 6/1991 | Shapiro | 128/735 |
| 5,086,770 | 2/1992 | Prangley | 607/88 |
| 5,150,704 | 9/1992 | Tatebayashi et al. | 606/10 |
| 5,250,068 | 10/1993 | Ideguchi et al. | 606/189 |
| 5,265,598 | 11/1993 | Searfoss et al. | 607/88 |
| 5,320,618 | 6/1994 | Gustaffsson | 606/9 |
| 5,337,741 | 8/1994 | Diamond | 600/8 |
| 5,405,357 | 4/1995 | Rowe-Lanzisera et al. | 606/204 |
| 5,441,531 | 8/1995 | Zarate et al. | 607/88 |
| 5,453,883 | 9/1995 | Chazallet | 359/890 |
| 5,472,415 | 12/1995 | King et al. | 623/16 |

FOREIGN PATENT DOCUMENTS

| | | | |
|---|---|---|---|
| 4009644 | 10/1991 | Germany | 128/907 |

OTHER PUBLICATIONS

M.E.D. Servi–Systems catalog 1997 Canadian device catalog pp. 13–19.
Photobiotics 1995 a book by Dr. Charles Mc Williams p. 114.

*Primary Examiner*—Jennifer Bahr
*Assistant Examiner*—Sonya Harris-Ogugua
*Attorney, Agent, or Firm*—Martin L. Stoneman

[57] ABSTRACT

An improved non-coherent pulsed and colored light stimulation device used for therapeutic effects in living creatures. Pulsed/colored light is applied to local areas, or acupuncture macro or micro systems, by means of a small diameter optic fiber (10) housed in a pen-like handpiece (18) which makes application comfortable and precise. The light source is an adjustable rate strobe (4) with a housing attached to the front (6) which allows color gel slides (12) to be interchanged. The light passes through the slides (12) and through a length of jacketed flexible optic fiber (10) where it becomes visible again at the radiant tip (20) of the handpiece (18).

19 Claims, 4 Drawing Sheets

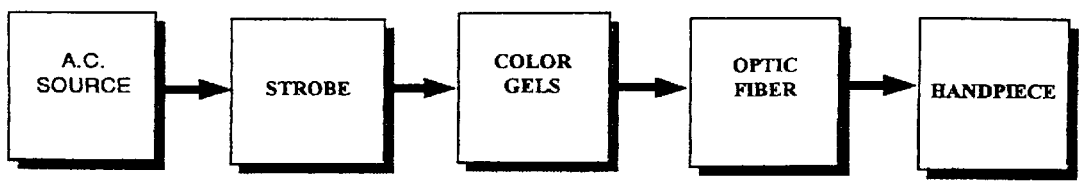
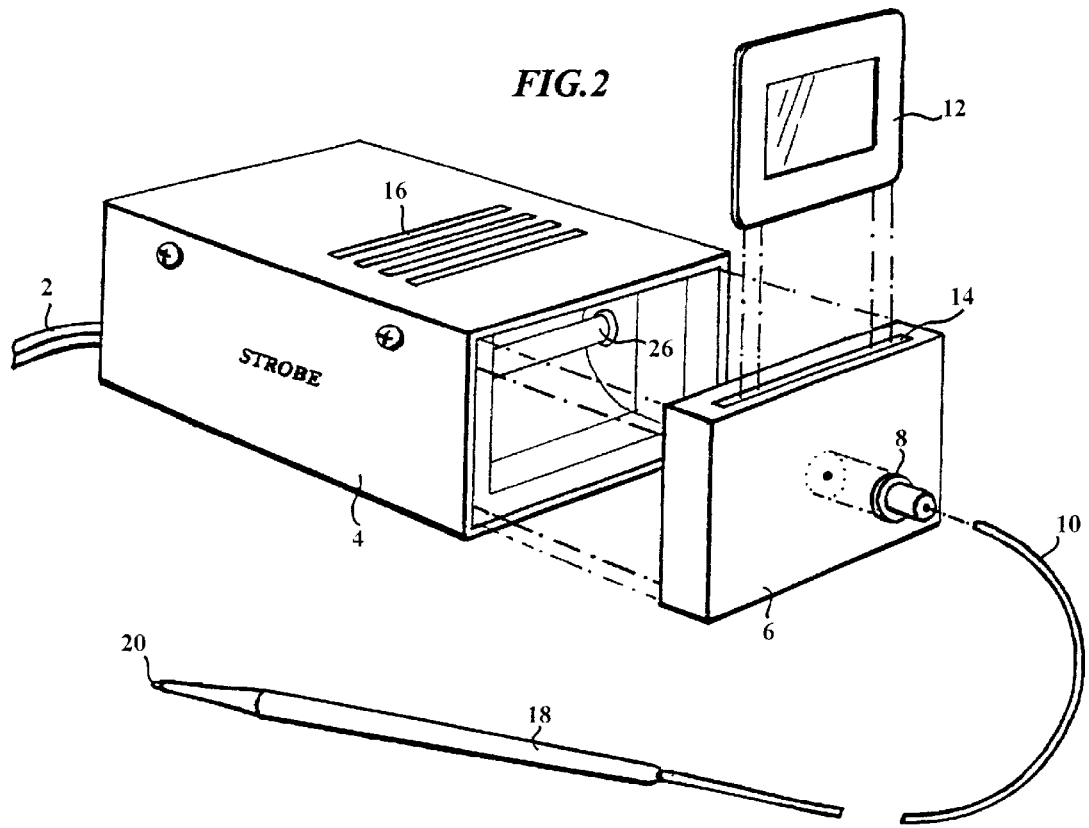

THERAPEUTIC DEVICE USING PULSED AND COLORED LIGHT

BACKGROUND

1. Field of the Invention

This invention relates to a pulsed/colored light stimulation device for therapeutic effects in living creatures. It is particularly applicable in body acupuncture, and ear or other micro-acupuncture systems.

2. Description of Prior Art

The stimulation of acupuncture points is carried out by needle insertion, electric current, moxibustion, pressure, and light.

Known light devices include diode lasers (coherent light), light emitting diodes (non-coherent light), incandescent light, and focused filtered sunlight.

Heretofore known embodiments of light applications are in the form of:

a. diffuse direct application of incandescent light
b. focused sunlight using a light focusing lens with filters
c. laser diode devices
d. L.E.D. (Light Emitting Diode) devices Direct application of incandescent light produces heat, and due to its broad range of radiation it may affect more than the desired areas of application and create undesirable results.

Sunlight obviously requires treatment out of doors, with the side effect of heating.

Lasers are bulky for use in the hand and expensive. They usually require the practitioner to be familiar with a number of output settings, pulse rates and widths, and stimulation modes which increase the treatment variables. This makes it difficult and time consuming to learn and use accurately.

Light Emitting Diodes are also bulky for use in the hand. The applicator body is cumbersome, and the embodiment of the electronic components produces some weight. The size of the tip of a LED which contacts the surface of the skin is much larger than an acupuncture point. When treatment of acupuncture micro-systems is preferred, such as ear acupuncture, the size of the illuminating tip is extremely important and should be as small as possible.

In addition LED's are not readily interchangeable. If a practitioner wishes to use more than one color or application tip, he must purchase another device, or struggle with electric leads. This is cumbersome and expensive.

LED's are only available in a limited variety of colors, thus treatment is confined to the use of available colors. Only a few colors are available in any LED acupuncture system. Very specific color frequencies have specific effects relative to body systems and organs. A variety of colors are required for practitioners to utilize these treatment principles.

Treatment time with light is proportional to the intensity of the light. The intensity of LED's is very low (0.5 mw to 5 mw). The lower the intensity the longer the treatment time required.

Repair of electronic equipment usually takes a long time. The time and money a practitioner loses as a result of equipment being repaired is unfortunate and frustrating. If an electronic device fails during a series of treatments the practitioner is forced to change modalities midstream. Unlike car repair, there are no rentals available as temporary replacements.

Heretofore known devices fall short in fulfilling the demonstrated need for a light stimulation device which:

Is light and comfortable in the hand
Is portable without requiring batteries
Can focus light in a very precise area
Can offer a complete range of color
Can allow for multiples (more applicators) at low price
Is economical to produce and purchase
Is easy to learn and use effectively
Can have parts replaced rather than being repaired Prior devices which apply light to the surface of the body have taken this area of therapeutics dramatically forward. Much information has been gleaned in clinical practice and in research regarding the use of light, color, and pulse. However no heretofore known device has combined these three elements in such an elegant and simple fashion as this invention.

OBJECTS AND ADVANTAGES

Accordingly, several objects and advantages of my invention are:

(a) to provide a light stimulation device which is most comfortable and easy to be manipulated by the hand and particularly when applying the radiant tip to difficult to reach body areas such as the inner folds of the ear.

(b) to provide a light stimulation device which has a very small diameter radiant tip which can address the requirements of micro-acupuncture systems.

(c) to provide a light stimulation device which can deliver an intense focused light in a very precise area on the surface of the skin.

(d) to provide a light stimulation device which makes an unlimited number of colors available through the use of color gels fitted into convenient plastic slide mounts.

(e) to provide a light stimulation device which can allow for the addition of low cost multiple applicator tips.

(f) to provide a light stimulation device with variable light pulse rates that are simple, easy to understand, and easy to utilize in treatment.

(g) to provide a light stimulation device that is practical, reliable and low cost.

(h) to provide a light stimulation device wherein the parts are easy to maintain, and replace if necessary at a very low cost without any time required for electronic repairs.

(i) to provide a light stimulation device which allows the practitioner to change colors rapidly and conveniently.

(j) to provide a light stimulation device which simplifies the art of applying light, pulse, and color to the skin, thereby making it easy to learn and use effectively.

(k) to provide a light stimulation device which offers radiant application tips in different diameters for various applications.

Further objects and advantages are to provide a light stimulation device which can be used to stimulate organ or tissue response when placed on areas of animal bodies other than the skin surface. Such areas would include but not be limited to mucous membranes, and the iris and sclera areas of the eye surface. Further objects and advantages of my invention will become apparent from a consideration of the drawings and ensuing description.

DRAWING FIGURES

FIG. 1 is a block diagram of this invention.

FIG. 2 is an exploded frontal perspective of one embodiment of this invention.

REFERENCE NUMERALS IN DRAWINGS

Figure 3:
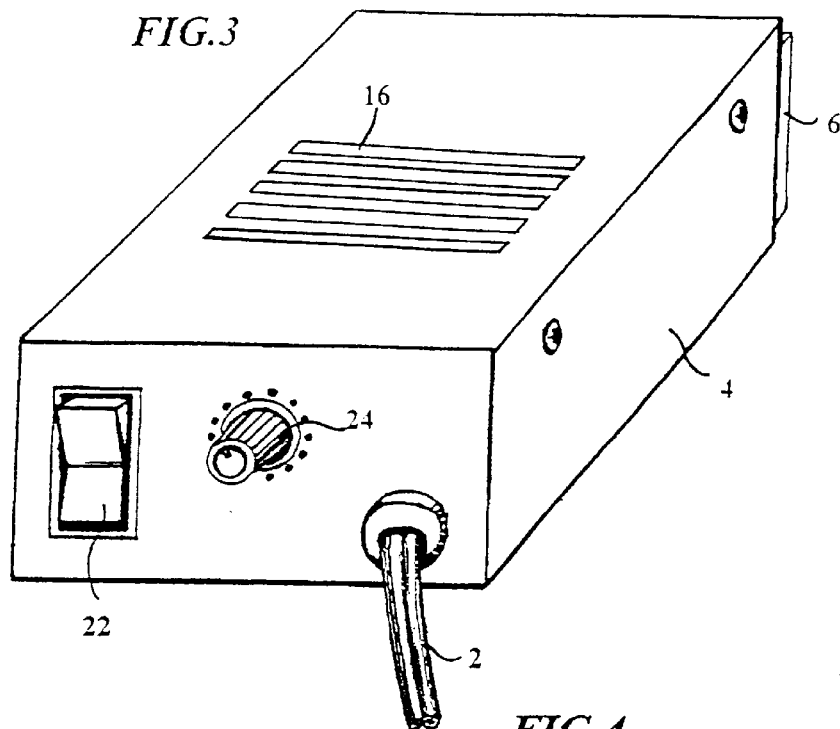
FIG. 3 is a rear perspective view of one embodiment of this invention.

| | |
|---|---|
| 2. A.C. source | 20. optic fiber tip |
| 4. strobe encasement | 22. on/off switch |
| 6. color gel slide housing | 24. pulse frequency adjustment dial |
| 8. optic fiber attachment button | 26. bulb |
| 10. jacketed optic fiber | 28. bulb reflector |
| 12. color gel slide | 30. light emitting diode |
| 14. color gel slide slot | 32. hand |
| 16. heat vent slots | 34. ear |
| 18. handpiece | 36. potentiometer |

SUMMARY

In accordance with the present invention a pulsed and colored light stimulation device to be used for therapeutic reasons on living creatures comprises an adjustable rate strobe light with a housing in front of the flash area to accommodate the insertion and removal of color gel slides, a length of optic fiber, and a handpiece. Light from the strobe passes through the color slide gel and into a length of optic fiber attached to the outside of the slide housing. At the end of the optic fiber is a handpiece to accommodate comfort, rigidity of the optic fiber, and precision in handling.

DESCRIPTION-FIGS. 1–9

FIG. 1 is a block diagram of the apparatus. The A.C. electrical current energizes the strobe light which passes through the color gel, then through the optic fiber where it emits pulsed and colored light at the tip of the handpiece.

FIG. 2 illustrates a typical embodiment of the apparatus. A color gel slide housing 6 is attached to the front of a strobe light to accommodate the insertion of color gel slides 12. The slide housing 6 is glued to the strobe encasement 4, but may be molded as part of the strobe encasement. A color gel slid slot 14 forms an opening at the top of the slide housing 6. There is also an opening at the bottom of the housing 6 to accommodate air flow to avoid overheating the slide 12. The color gel slide slot 14 is required to be slightly larger than the color gel slide 12 so the slide 12 may be inserted and removed easily. To keep the apparatus lightweight it is preferred that the slide housing 6 and the strobe encasement 4 are made of plastic. The strobe encasement 4 would also be vented at the top 16 and bottom to avoid overheating of the apparatus.

A preferred length of flexible optic fiber 10 is from six to eight feet, however not limited to that length. Since there is very little light intensity loss at 80 meters, the length is therefore not limited by intensity variables. The diameter of the jacketed optic fiber in the preferred embodiment is 2.20 mm for micro work but may be 3–4 mm. or larger. In the preferred embodiment the optic fiber jacket material is black polyethylene, and the core is single strand acrylic polymer—available from Edmund Scientific, Barrington, N.J. The optic fiber 10 is attached to the slide housing 6 by a plastic attachment button 8. A hole the same diameter as the optic fiber 10 is drilled through the slide housing 6 and the optic fiber 10 is inserted all the way through the button 8 and into the hole in the slide housing 6 allowing light from the strobe to pass into the optic fiber. The optic fiber 10 is glued in place, but may remain in place through friction or an attachment which allows for the optic fiber 10 to be interchangeable with optic fibers of different diameters.

The preferred handpiece 18 is made of a two-piece molded plastic, but may be made of any material which is rigid, and can be drilled, or molded with a hole in the center. The optic fiber 10 passes from the slide housing 6 through a hole in the length of the handpiece and protrudes 1.5 mm beyond the end of the handpiece 18. This protruding part of the optic fiber 10 is the tip 20 and may protrude at varying lengths. The tip 20 should be rounded to avoid any scratchy surface.

The color gel slides 12 are assembled from Roscolene color filters available from Samarco in Dallas Tex. One or more gel filters are cut to size and inserted in 24×36 glassless slide mounts to create the color gel slide 12. After the gel filters are inserted into the plastic slide mounts they should be glued. Roscolene color gel filters are used either alone or in combination in a plastic slide mount to obtain variations of color.

FIG. 3 depicts a rear perspective of the strobe encasement 4. Depicted is an on/off switch 22, an A.C. power cable 2, and a pulse frequency adjustment dial 24. The pulse frequency in the preferred embodiment ranges from zero to ten pulses per second.

Strobe lights are available in a variety of sizes and intensities. Small strobes required for this application are very inexpensive. Many suppliers are listed in the Thomas Register. The preferred embodiment strobe is supplied by Visual Effects Inc., Brooklyn, N.Y.

Figure 4:
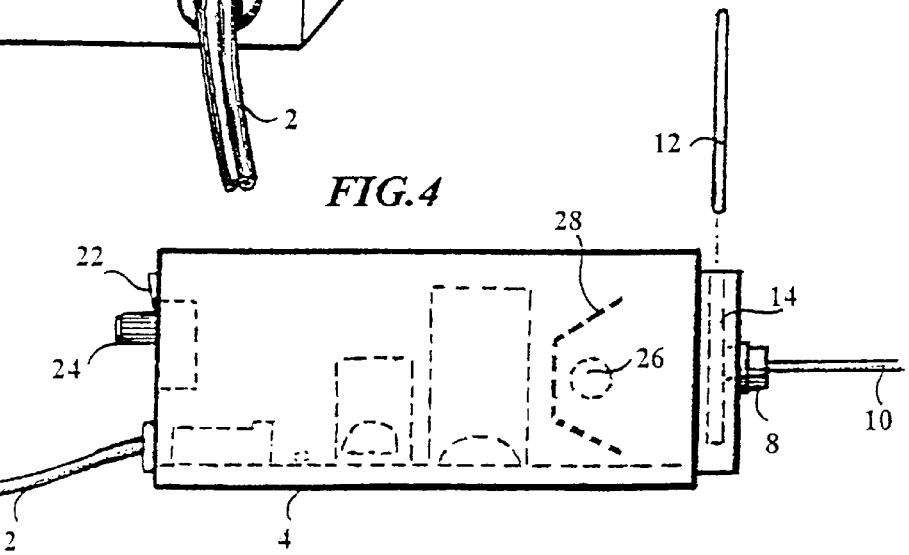
FIG. 4 is a side view of one embodiment of this invention.

FIG. 4 is a side view and depicts a bulb 26 inside the encasement which in the preferred embodiment is an eight watt Xenon bulb, however other bulbs and intensities may be utilized. A bulb reflector 28 to the rear of the bulb in the encasement, directs the light forward toward the slide housing 6 and optic fiber 10. FIG. 4 also depicts the slot in the slide housing 6 in which the color gel slide 12 is placed. An alternative embodiment could include a light focusing lens placed between the color gel slide 12 and the optic fiber 10.

Figure 5:
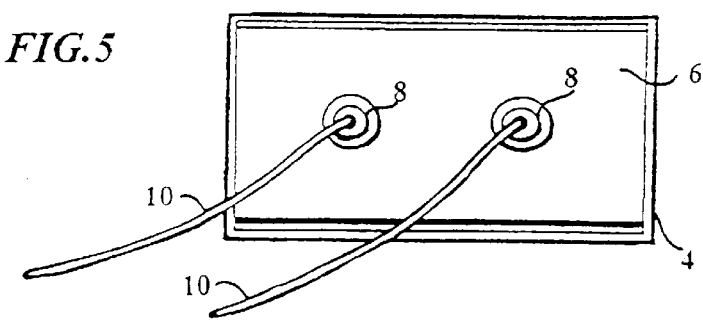
FIG. 5 is a frontal view of this invention with multiple fiber optic attachments as an alternative embodiment.

FIG. 5 illustrates an alternative embodiment containing multiple optic fibers 10 and multiple optic fiber attachment buttons 8 at the front of the color gel slide housing 6.

Figure 6:
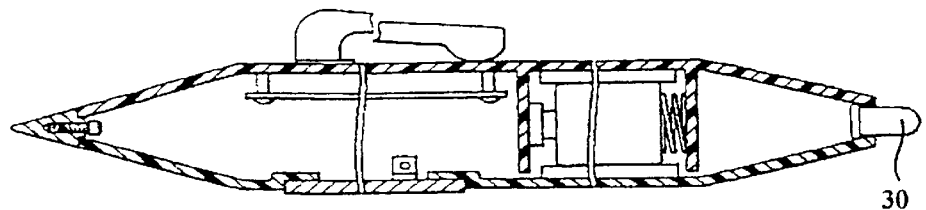
FIG. 6 is a view of a prior art embodiment using a Light Emitting Diode
Figure 7:
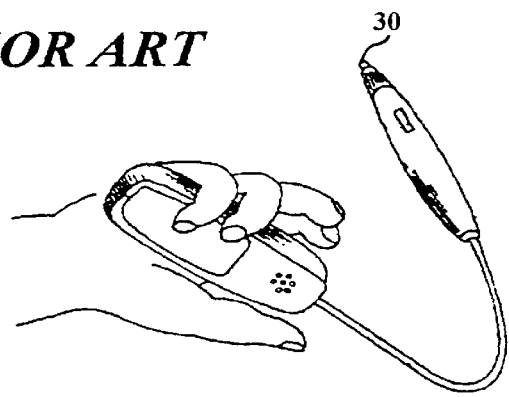
FIG. 7 is another view of a prior art embodiment using a Light Emitting Diode.

FIG. 6 and FIG. 7 illustrate the embodiments of prior art pulsed light stimulation devices which are designed to fit in the hand. Depicted are light emitting diodes 30 for comparison to the optic fiber tip 20 in FIG. 8. The advantages of my light stimulation device become obvious when considering ease of use and the requirements of micro acupuncture.

Figure 8:
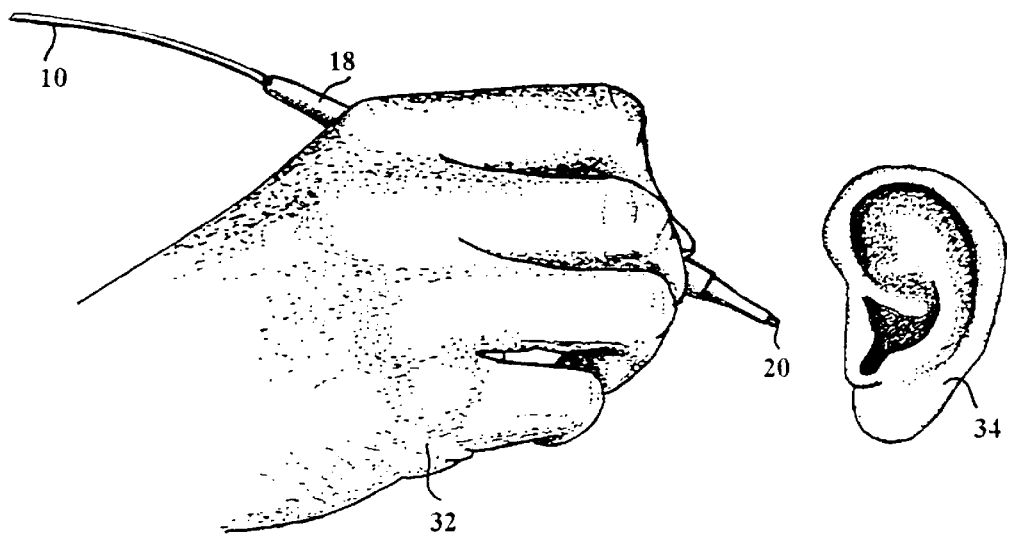
FIG. 8 illustrates how the handpiece is used and its relationship to the ear.

FIG. 8 illustrates a hand 32 with the handpiece 18 as it would be used in treating a subject, and an ear 34. The hand 32 and ear 34 are in accurate proportions to each other and as they would be on an actual subject. They illustrate the requirement for a small diameter tip 20.

Figure 9:
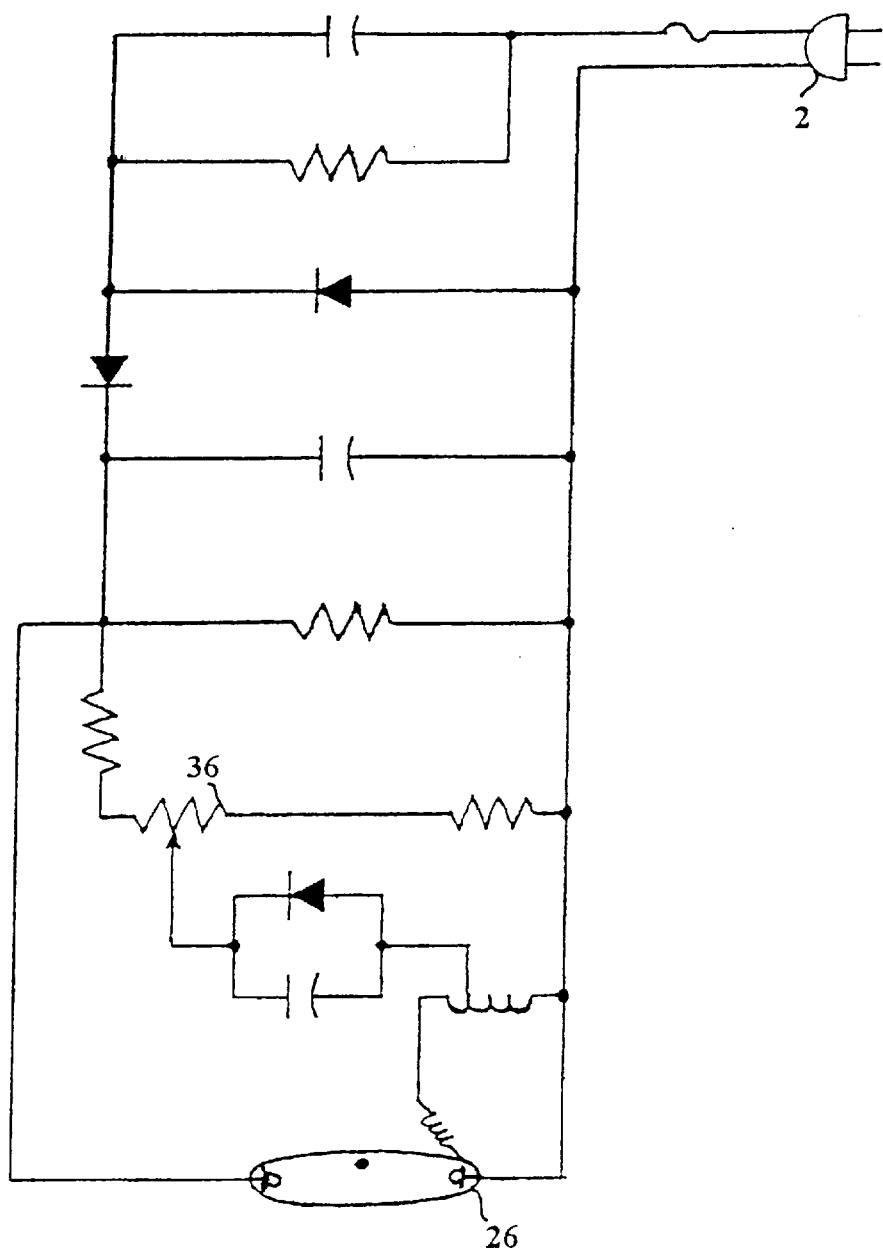
FIG. 9 is a schematic of the strobe light circuit.

FIG. 9 is the preferred embodiment's schematic diagram of the strobe light. The A.C. supply 2 builds a charge in a capacitor. When the capacitor discharges the bulb 26 flashes. The discharge is controlled by a R.C. (resistor/capacitor) time constant. The potentiometer 36 alters the R.C. time constant, thus changing how fast or slow the bulb 26 flashes.

OPERATION-FIGS. 2, 3, 8

The manner of using the light stimulation device with a fiber optic tip 20 is similar to that for devices using light emitting diodes. Namely, one places the illuminant end of the device on the area to be treated, whether it be an injured, painful part of the body, or an acupuncture point. One advantage of this device is that the duration of treatment time may be less because the intensity of the light at the illuminant end is greater. The fiber optic illuminant tip 20 in addition allows treatment at the corneal surface of the iris, and sclera of the eye. In such treatment the surface is not touched, but approached to initiate an organ or tissue response.

To begin, the on/off switch 22 is set to the "on" position and the pulse frequency adjustment dial 24 is set to the practitioner's preferred rate. It has been observed that the various body pulses become entrained (harmonized) with rates being set between six and eight pulses per second. This entrainment allows for a greater therapeutic effect of the light and color.

Once the device is on and pulsing, the practitioner chooses a particular color slide 12 aimed at creating particular organ or tissue responses, and inserts it into the slide slot 14 on the slide housing 6. The effect at the illuminant tip is a bright, colored, and pulsed light. No heating has been observed at the tip 20 using the device in the preferred embodiment. The actual brightness of the tip 20 is dependent on the light density of the color filters themselves.

An advantage of this device is that as the practitioner approaches the subject, the flexible length of optic fiber 10 allows him to move about the subject with freedom, unencumbered by electronic devices. If during treatment the practitioner chooses to use any micro acupuncture systems such as the ear, then he would find this device exceptionally suited to reaching difficult and small areas as well as having tight and precise control of tip 20 placement.

Treatment time is from fifteen seconds to three minutes per point or area being treated. Usually a number of points are treated in succession. The lightweight handpiece 18 and speed by which the color slides 12 can be interchanged are advantages of this invention.

Unlike many other light stimulation devices, the practitioner may begin using this device immediately. The simplicity and elegance of the theory and operation mean that the practitioner is not required to take classes, watch videos, or read difficult manuals in order to effectively treat patients.

When treatment is terminated the color slides 12 are removed and the device is turned off 22. If any part fails or is damaged it may be immediately replaced without the usual time required for electronic repair. All of the parts, including the strobe are so inexpensive as to make electronic repair impractical. All parts can be replaced overnight when required.

SUMMARY, RAMIFICATIONS, AND SCOPE

Accordingly, the reader will see that this improved therapeutic device using pulsed light and color can be used more economically, more comfortably, and more precisely than any present light stimulation device. In addition, due to the extremely large color range of available gels, all theories and paradigms relative to color therapy may be explored by the practitioner. Furthermore, this invention has the additional advantages in that it provides an ability to place the radiant tip accurately on any location of a subject's body;

it allows for speedy parts replacement without a waiting period for electronic repair;

it allows the practitioner to use utilize the handpiece unencumbered by an accompanying electronic device since the optic fiber allows the light generating device (strobe) to be placed at a distance;

it provides freedom from using and replacing batteries, and the possibility that they may fail during use. In addition, it insures that the light intensity remains constant whereas light intensity may diminish as batteries weaken;

it allows the practitioner immediate and effective use without having to endure a long or difficult learning period;

it allows availability to a widespread population due to its practical use and low cost;

it provides the opportunity for a practitioner to use multiple radiant treatment tips without the necessity of purchasing more devices;

it allows for rapid changing of colors. Practitioners use various colors in succession to achieve therapeutic treatment, and this invention allows them to insert and remove color slides rapidly.

Although the description above contains many specificities, these should not be construed as limiting the scope of the invention but as merely providing illustrations of some of the presently preferred embodiments of this invention. For example, the optic fiber length may vary, the optic fiber may vary in diameter, the optic fiber may consist of one single strand or multiple strands, the apparatus may be equipped with a light focusing lens between the color slide and the optic fiber for the purpose of further increasing the light and color intensity, the casing materials for the slide housing and the strobe encasement may be of metal etc., the bulb may be of a different wattage or composition, the connection of the optic fiber to the slide housing may be permanent or interchangeable, and it may be made of extruded plastic or molded, etc., the handpiece may be made of other materials such as wood, metal, etc.

Thus the scope of the invention should be determined by the appended claims and their legal equivalents, rather than by the examples given.

I claim:

1. A therapeutic light device comprising:

(a) a pulsed light generator having a light emitting end;

(b) a plurality of color gel slides;

(c) a housing into which each said color gel slide may be inserted or removed;

(d) a means of connecting said housing to the light emitting end of said pulsed light generator, whereby light passes through said color gel slides;

(e) a flexible jacketed optic fiber of predetermined diameter and of sufficient length to accommodate use by a human, said flexible jacketed optic fiber having an applicator end and an illuminant tip;

(f) a means of connecting said optic fiber to a hole in said housing, whereby colored light passes into said optic fiber;

(g) an elongated handpiece, having a handpiece end which surrounds and encases the applicator end of said flexible jacketed optic fiber, leaving said illuminant tip of said optic fiber to protrude past said handpiece end of said handpiece sufficiently to accommodate treatment of living creatures, whereby said handpiece provides an enlarged means for holding said optic fiber conveniently.

2. The light device of claim 1 wherein said pulsed light generator comprises a strobe.

3. The light device of claim 2 wherein said strobe is constructed and arranged to provide light pulse frequencies up to 10 pulses per second.

4. The light device of claim 2 wherein said strobe comprises a xenon bulb.

5. The light device of claim 4 further comprising:

(a) intensity means for varying the intensity of said strobe;

(b) wherein said intensity is varied by installing different wattages of said xenon bulb.

6. The light device of claim 2 wherein the material of the jacket of said optic fiber comprises black polyethylene, and the material of the core of said optic fiber comprises single strand acrylic polymer.

7. The therapeutic light device of claim 2 further comprising multiple said means of connecting a said optic fiber to said housing and multiple associated said handpieces, whereby one can utilize multiple optic fibers for treatment while using only one said pulsed light generator.

8. The light device of claim 1 further comprising:

(a) group means for facilitating user selection of a said color gel slide;

(b) wherein said group means comprises a predetermined multitude of colors of said plurality of said color gel slides.

9. The therapeutic light device of claim 1 wherein a light focusing lens is placed between said color gel slides and said optic fiber whereby light intensity received by said optic fiber is increased.

10. A therapeutic light system comprising:

(a) light source means for providing a pulsed non-coherent light;

(b) color means for providing a first chromatic adjustment of said non-coherent light to provide a colored non-coherent light;

(c) variation means including a plurality of different color gel structures, separately applied for providing a user-chosen selection among multiple said chromatic adjustments; and (d) optic fiber means for transporting said colored non-coherent light to a position immediately adjacent a living creature.

11. A therapeutic light system according to claim 10 wherein said light source means comprises a strobe light.

12. A therapeutic light system according to claim 11 wherein said strobe light comprises an adjustable rate strobe light.

13. A therapeutic light system according to claim 11 wherein said color means comprises a color gel slide.

14. A therapeutic light system according to claim 13 wherein said variation means comprises:

(a) slide holding means for holding a color gel slide; and (b) a plurality of different color gel slides, each said different color gel slide being structured and arranged for selective user placement within said slide holding means.

15. A therapeutic light system according to claim 11 wherein said optic fiber means comprises:

(a) a flexible jacketed optic fiber having a first end and a second end;

(b) means for passing said colored non-coherent light into said first end of said flexible jacketed optic fiber; and (c) handpiece means grippable by a user for holding a portion of said flexible jacketed optic fiber adjacent said second end of said flexible jacketed optic fiber in such manner that said second end of said flexible jacketed optic fiber extends from said handpiece means so as to permit touching of said living creature;

(d) said optic fiber means being structured and arranged in such manner that said colored light may pass directly from said second end of said flexible jacketed optic fiber onto said living creature.

16. A therapeutic light system according to claim 15 wherein said handpiece means comprises a pen-like shape.

17. A therapeutic light system according to claim 15 wherein said second end of said flexible jacketed optic fiber extends from said handpiece means a distance of about 1.5 millimeters.

18. A therapeutic light system according to claim 11 wherein said optic fiber means comprises multiple separate optic fibers, each respective said separate optic fiber being structured and arranged to transport said colored non-coherent light to a separate respective position immediately adjacent a living creature, whereby multiple treatment locations may be utilized using only one said light source means.

19. A method for using a therapeutic light system for treating a living creature, comprising the steps of:

(a) providing a pulsed strobe light of user-selected intensity to provide non-coherent light;

(b) setting said pulsed strobe light to pulse at a frequency of no more than ten pulses per second;

(c) selecting a color gel slide from a group of said color gel slides each of different color;

(d) passing said non-coherent light through said selected color gel slide to provide colored non-coherent light;

(e) passing said colored non-coherent light into a first end of a flexible jacketed optic fiber;

(f) passing said colored non-coherent light through said flexible jacketed optic fiber to a second end of said flexible jacketed optic fiber having an applicator end and an illuminant tip; and (g) passing said colored non-coherent light from said second end of said flexible jacketed optic fiber directly onto said living creature by said illuminant tip, said tip being in contact with tissue of the living creature.

\* \* \* \* \*